United States Patent [19]

Plat et al.

[11] 4,021,430
[45] May 3, 1977

[54] DIHYDROAPOVINCAMINIC ACID AMINES

[75] Inventors: Michel Marie René Plat; Monique Plat born Berry, both of Antony, France

[73] Assignee: Synthelabo, Paris, France

[22] Filed: June 26, 1974

[21] Appl. No.: 483,351

[30] Foreign Application Priority Data

June 19, 1974 France .............................. 74.21210

[52] U.S. Cl. ...................... 260/293.53; 260/243 B; 260/247.5 EP; 260/268 PC; 424/248.54; 424/267
[51] Int. Cl.² ......................................... C07D 57/08
[58] Field of Search ................................ 260/293.53

*Primary Examiner*—Paul J. Killos
*Attorney, Agent, or Firm*—Stevens, Davis, Miller & Mosher

[57] ABSTRACT

16,17-Dihydroapovincaminic acid amides of the general formula:

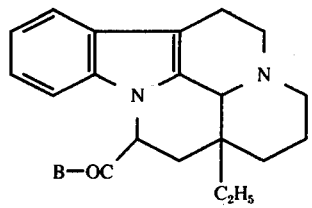

wherein B is an $-NR_1R_2$ group wherein $R_1$ is a hydrogen atom or a saturated or unsaturated, linear or branched $C_{1-4}$ aliphatic hydrocarbon group, and $R_2$ is a saturated or unsaturated, linear or branched $C_{1-4}$ aliphatic hydrocarbon group, a phenyl $C_{1-4}$ alkyl or a cycloalkyl $C_{1-4}$ alkyl group; or B is a

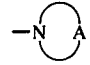

group wherein A is a saturated $C_{4-6}$ alkylene group which may be interrupted by a hetero-atom; or a pharmaceutically acceptable acid addition salt thereof which are useful for the treatment of cardiovascular disorders, and a method for their preparation.

3 Claims, No Drawings

DIHYDROAPOVINCAMINIC ACID AMINES

The present invention relates to new dihydroapovincaminic acid amides and pharmaceutically acceptable acid additions salts thereof, to the preparation of such compounds and to pharmaceutical compositions containing them.

The compounds according to the invention correspond to the general formula (I)

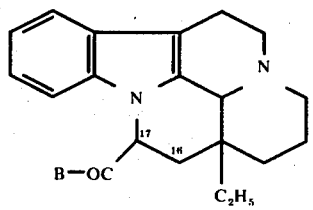

(I)

wherein B is an $-NR_1R_2$ group wherein $R_1$ is a hydrogen atom or a saturated or unsaturated, linear or branched $C_{1-4}$ aliphatic hydrocarbon group, and $R_2$ is a saturated or unsaturated, linear or branched $C_{1-4}$ aliphatic hydrocarbon group, a phenyl-or a cycloalkyl-$C_{1-4}$ alkyl group; or B is an

group wherein A is a saturated $C_{4-6}$ alkylene group which may be interrupted by a hetero-atom. Examples of suitable hetero-atoms are oxygen or sulphur or a group $-N(R)-$ wherein R is a hydrogen atom or a $C_{1-6}$ alkyl group.

By way of example,

can denote pyrrolidine, piperidine, perhydroazepine, morpholine, thiomorpholine, piperazine, or N-methylpiperazino. Moreover, the alkylene chain can carry, in any position, one or more $C_{1-6}$ alkyl substituents.

The compounds of the invention form addition salts with pharmaceutically acceptable acids, and these addition salts form part of the invention.

The compounds of the present invention can be prepared by the general methods for the synthesis of amides. One such method involves reacting dihydroapovincaminic acid or one of its functional derivatives with an amine.

For example dihydroapovincaminic acid or one of its alkali metal salts can be converted to an acid halide, e.g. by means of an oxalyl halide, in particular oxalyl chloride, or by means of a thionyl halide or a halogenated derivative of phosphorus. This reaction is preferably performed at room temperature in a non-polar solvent, for example an aromatic hydrocarbon such as benzene, toluene or xylene. An acid acceptor, e.g. a tertiary organic base such as pyridine may also be present. The acid halide can be isolated from the solvent, or used as such for the next step.

The conversion of this acid halide to an amide is carried out by reacting the acid halide with a particular amine, under hot conditions, in a neutral or preferably basic medium, optionally in the presence of a tertiary organic base.

A variant of the above process consists in converting dihydroapovincaminic acid into its alkyl ester, which is then reacted with an amine to obtain the desired amide.

The present invention also provides pharmaceutical compositions containing a compound of general formula (I) or a pharmaceutically acceptable acid addition salt thereof and a pharmaceutically acceptable carrier or diluent.

The compositions are preferably administered orally, endorectally, parenterally or topically and may also contain other active substances with which the compounds of the present invention are pharmacologically and therapeutically compatible.

Any of the usual forms suitable for oral administration may be used, such as tablets, dragees, gelatin-coated pills, capsules, sachets and potable solutions or suspensions. The unit dose of active compound may vary from 0.5 to 25 mg and the daily dosage may be 0.5 to 200 mg.

For endorectal administration, unit administration is effected at a dosage of 1 to 50 mg, the active principle being distributed throughout any excipient which is known as a base for suppositories. From 1 to 4 suppositories are administered each 24 hours.

Solutions which have been prepared beforehand or at the time of use, buffered to the physiological pH, useful for parenteral use and contain 0.5 to 20 mg of active principle in 1 to 5 ml. In practice, they are dispensed in 1 to 5 ml ampoules for intramuscular or intravenous administration or for administration by slow intravenous infusion. The daily dose administered parenterally is usually 0.5 to 100 mg.

For topical administration, lotions, emulsions, ointments or creams which promote cutaneous penetration are used.

The compounds of the present invention are useful in human and veterinary therapy, particularly in the cardiovascular field. They are, in particular, coronary dilators and peripheral and cerebral vasodilators and, consequently, hypotensive agents. They are particularly useful in the field of cerebral circulation, because they very particularly improve the flow rate of blood through the brain and the use of oxygen by this organ. Furthermore, they are in general, cellular oxygenators.

The following Examples serve to illustrate the invention. Melting points are determined on a Kofler block.

EXAMPLE 1

16,17-Dihydro-apovincaminic acid diethylamide and its hemi-malate ($R_1 = R_2 = C_2H_5$; code number SLB-829 B)

Oxalyl chloride (3.69 g, 2.50 ml; 0.027 mol) was added to a suspension of dihydroapovincaminic acid (8.900 g; 0.027 mol) in anhydrous benzene (150 ml). in a flask. The flask was sealed with a calcium chloride guard tube and the mixture was left to stand in the dark while stirring for 1¼ hours. The resultant precipitate was filtered off, and anhydrous diethylamine (15 ml) was added, in portions, to the filtrate which was kept in an ice bath. The resultant mixture was stirred for 5 hours, filtered and the filtrate was distilled to dryness under reduced pressure. The residue obtained was a thick brown-yellow oil. Thin layer chromatography (neutral silica; elution with chloroform/methanol, 95.5) reveals the presence of one main compound, (Rf 0.20) accompanied by a few impurities.

The crude amide was dissolved in a minimum amount of chloroform and the solution obtained was mixed with a sufficient amount of alumina to form a slurry. The solvent was then removed from the slurry by distillation under reduced pressure and the resulting adsorbate was introduced at the top of a column of neutral alumina (300 g) of activity 1, which was eluted with ether (300 ml).

A chromatographically pure compound (3.32 g; 32% yield) which crystallised on simply concentrating the ether, was obtained. Melting point: 148°–150° C;

Analysis—Calculated%: C=75.95; H=8.76; N=11.07; O=4.22. Found %: C, 76.01; H, 8.69; N, 11.10; O, 4.30.

U.V. (neutral ethanol) $\lambda_{max}$. nm (log$\epsilon$)=284 (3.87), 293 (8.82);

I.R. 1615–1630 cm$^{-1}$ (C=O amide);

N.M.R. (ppm) 1.00 (triplet, $C_{21}$-methyl group), 1.15 (2 triplets, N($CH_2$—$CH_3$)$_2$), 3.50 (2 quartets, N($CH_2$—$CH_3$)$_2$), 4.94 (1 quartet, axial H in the α-position to

The amide was converted to its hemi-malate by treatment with malic acid in warm methanol. The salt is an amorphous white powder which is soluble in water, methanol and acetone. It melts at 95°–96° C.

Analysis—Calculated %: C=65.48; H=7.65; N=8.18; O=18.69. Found %: C, 65.56; H, 7.69; N, 8.20; O, 18.59.

EXAMPLE 2

16,17-Dihydroapovincaminic acid β-phenethylamide and its hemi-malate ($R_1$ = H, $R_2$ = $C_6H_5$—$CH_2$—$CH_2$—; code number SLC-825)

Oxalyl chloride (2.15 g, 1.46 ml; 0.017 mol) was added to a suspension of dry dihydroapovincaminic acid (5.525 g; 0.017 mol) in anhydrous benzene (250 ml) in a flask. The flask was sealed with a calcium chloride guard tube. The mixture was left to stand in the dark, while stirring, until the acid has completely dissolved (approximately 1¾ hours). Phenethylamine (6.5 ml; 3 mols) was added. A precipitate formed instantaneously. The mixture was then left in contact for 2 hours. Ammonia (5% solution) was added to the mixture until it was alkaline and then the mixture was extracted with chloroform. The chloroform extract was washed twice with water, dried over anhydrous magnesium sulphate filtered and evaporated to dryness to give a yellow oil (13.49 g). Thin layer chromatography (silica; elution using chloroform/methanol, 90/10) showed the presence of one main compound, Rf=0.67.

The crude oil was dissolved in the minimum amount of chloroform and the resultant solution mixed with a sufficient amount of alumina to form a slurry. The solvent was distilled off the slurry under reduced pressure and the resulting adsorbate introduced at the top of a column of neutral alumina (400 g) and eluted with ether (500 ml portion).

The ether eluate yielded a chromatographically pure compound (5.83 g; 80% yield), which crystallised on simply concentrating the ether and had a melting point of 189°–190° C.

Analysis — Calculated %: C, 78.65; H, 7.78; N, 9.83; O, 3.74. Found %: C, 78.60; H, 7.80; N, 9.76; O, 3.80.

U.V. (ethanol) $\lambda_{max}$ nm (log$\epsilon$) = 210 (4.50);

I.R. (KBr) 3250 (NH), 1645 (amide) cm$^{-1}$;

N.M.R. (CDCl$_3$, $\delta_{T.M.S.}$ = O, ppm) 1.00 (triplet, ethyl), 3.60 (1 quartet, N—$\underline{CH}_2$), 4.53 (1 quartet; $H_{16}$, $J_{aa}$ = 12 Hz, Jde = 5.5 Hz), 6 (broad signal; —$\underline{NH}$—).

5.630 g of the amide which had not been recrystallised but which was pure by thin layer chromatography were dissolved in warm methanol (300 ml). A solution of malic acid (1.766 g; 1 mol) in methanol (20 ml) was added. After leaving the mixture to stand for 5 minutes, the methanol was distilled off to give the hemi-malate of 16,17-dihydroapovincaminic acid β-phenethylamide (7.35 g, 98% yield) as an amorphous white compound of melting point 119°–120° C.

Analysis — Calculated %: C, 68.40; H, 6.90; N, 7.40; O, 17.10. Found %: C, 68.36; H, 7.04; N, 7.53; O, 17.16.

EXAMPLE 3

Piperidinyl-16,17-dihydroapovincamide and its hemi-malate (A = ($CH_2$)$_5$; code number SLB 831)

Oxalyl chloride (9.5 g; 0.075 mol) was added to a suspension of 16,17-dihydroapovincaminic acid (23.3 g; 0.075 mol) in anhydrous benzene (21). This suspension was stirred for 15 hours, and then anhydrous pyridine (5 ml) followed by freshly distilled piperidine (7 g; 0.075 mol) was added. The resultant solution was heated under reflux for 1 hour and then the solvent was evaporated in vacuo on a water bath. The residue was dissolved in water (1 l.), the solution was rendered alkaline with ammonia and extracted several times with ether. The combined ether extracts were dried over sodium sulphate, filtered and the ether removed to give crystalline piperidinyl-16,17-dihydroapovincamide (11.1 g), melting point: 162°–165° C, [α]578/20 = +39° (alcohol, c = 1).

Analysis: $C_{25}H_{33}ON_3$ — Calculated %: C, 76.68; H, 8.50; O, 4.09; N, 10.73. Found %: C, 76.65; H, 8.52; O, 4.16; N, 10.76.

By contacting equimolecular amounts of malic acid and the above compound, piperidinyl-16,17-dihydroapovincamide hemi-malate was obtained; melting point = 130°–133° C.

Analysis: $C_{29}H_{39}O_6N_3$ — Calculated %: C, 66.26; H, 7.48; N, 7.99; O, 18.26. Found %: C, 66.32; H, 7.46; N, 7.91; O, 18.19.

EXAMPLE 4

Morpholinyl-16,17-dihydroapovincamide and its hemi-malate (A = ($CH_2$)$_2$O($CH_2$)$_2$; code number SLB 829)

Oxalyl chloride (6.35 g; 0.05 mol) was added to a suspension of 16,17-dihydroapovincaminic acid (16.2 g; 0.05 mol) in anhydrous benzene (1.5 l). This suspension was left to stand for 15 hours, with stirring, at room temperature, and then morpholine (4.4 g; 0.05 mol) was added. The mixture was left to stand for 5 hours; the benzene was evaporated in vacuo on a water bath. The residue was triturated in methylene chloride and the mixture filtered. The solvent was evaporated from the filtrate and the residue purified by passage through a column of alumina (200 g) in ether. Morpholinyl-16,17-dihydroapovincamide was obtained in the form of crystals which melt at 222°–224° C [α] 22°/578 = + 40° (chloroform, c = 1).

Analysis: $C_{28}H_{37}N_3O_7$ — Calculated %: C, 73.25; H, 7.94; O, 8.13; N, 10.68. Found %: C, 73.21; H, 7.92; O, 8.19; N, 10.73.

By contacting equimolecular amounts of malic acid and the above base, morpholinyl-16,17-dihydroapovincamide hemi-malate was obtained; melting point = 134°–137° C.

Analysis: $C_{28}H_{37}N_3O_7$ — Calculated %: C, 63.74; H, 7.07; O, 21.23; N, 7.97. Found %: C, 63.69; H, 7.08; O, 21.30; N, 7.90.

EXAMPLE 5

The hemi-malates of the compounds of Examples 1 3 and 4 (SLB - 829 B, SLA-831 and SLA-829) were tested on male rabbits. Vincamine was used as a comparison.

The experimental technique used was cerebral oedema in male rabbits of the "crossed wild-rabbit" species, which had fasted for 18 hours.

The animals were divided into 7 batches and were treated by intraduodenal administration of a composition containing the test substances in the amounts shown in the following Table:

TABLE

| Group | Test Compound | Number of animals | Volumn of solution (administered) (ml/kg) | Amount of test Compound (mg/kg) | Ascorbic acid (mg/kg) |
|---|---|---|---|---|---|
| I | Control | 8 | 2 | — | 10.0 |
| II | SLB 829-B | 8 | 2 | 1.25 | 2.5 |
| III | SLB 829-B | 3 | 2 | 2.5 | 5.0 |
| IV | SLB 829-B | 4 | 2 | 5.0 | 10.0 |
| V | SLA 829 | 8 | 2 | 5.0 | 10.0 |
| VI | SLA 831 | 8 | 2 | 5.0 | 10.0 |
| VII | Vincamine | 8 | 2 | 5.0 | 10.0 |

Twenty-four hours before the test, the animal was prepared for an electrocephalogram. A reference trace was recorded and then the unilateral excision of a bone flap was performed.

Twenty-four hours later, after recording a new trace, the dura mater was opened up and this caused an oedema to form (hernia of the cortex, with greater or lesser compression of the adjacent sub-cortical structures and repercussions relating to the contralateral hemisphere), leading to profound changes, and particularly disturbances of the theta rhythm.

The treatment was carried out one hour later, and the electrocorticographic recording was followed for 6 hours.

It should be noted that the general tolerance was good. The results were as follows:

SLB 829.B: The duration of the curative effect of this compound does not seem to be directly related to the dosage administered, since for a dosage of 1.25–2.5 and 5 mg/kg it lasts for approximately 6 hours, on average. The therapeutic effect obtained with a dosage of 1.25 mg/kg of the compound is similar in intensity and in duration to that observed with 5 mg/kg of vincamine.

SLA 829: This compound gives an immediate and intense beneficial effect. At the same dose, it has a definite advantage over vincamine, because it acts more rapidly and for a longer time (48 hours).

SLA 831: This compound is a little less active.

In conclusion, although the compound SLB-829-B does not act over such a long period as SLA-829, it is nevertheless superior to the latter, because the effective dosage is four times lower.

We claim:

1. A compound of the general formula:

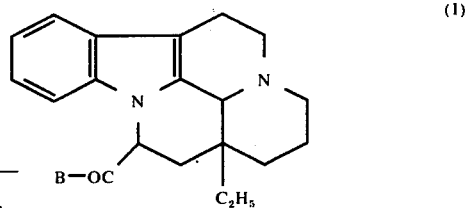

(I)

wherein B is an —$NR_1R_2$ group wherein $R_1$ is a hydrogen atom or a saturated or unsaturated, linear or branched $C_{1-4}$ aliphatic hydrocarbon group, and $R_2$ is a saturated or unsaturated, linear or branched $C_{1-4}$ aliphatic hydrocarbon group, a phenyl $C_{1-4}$ alkyl or a cycloalkyl $C_{1-4}$ alkyl group; or a pharmaceutically acceptable acid addition salt thereof.

2. A compound as claimed in claim 1 which is 16,17-dihydro-apovincaminic acid diethylamide or its hemi-malate.

3. A compound as claimed in claim 1 which is 16,17-dihydro-apovincaminic acid β-phenethylamide or its hemi-malate.

* * * * *